US00PP16556P2

(12) United States Plant Patent
Bernuetz

(10) Patent No.: US PP16,556 P2
(45) Date of Patent: May 16, 2006

(54) *ARGYRANTHEMUM* PLANT NAMED 'OHMADMADE'

(50) Latin Name: *Argyranthemum×hybrida*
Varietal Denomination: OHMADMADE

(75) Inventor: Andrew Bernuetz, Silverdale (AU)

(73) Assignee: Bonza Botanicals Pty. Ltd., Sydney (AU)

( * ) Notice: Subject to any disclaimer, the term of this patent is extended or adjusted under 35 U.S.C. 154(b) by 48 days.

(21) Appl. No.: 11/011,322

(22) Filed: Dec. 13, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Buchanan Ingersoll PC

(57) ABSTRACT

A new and distinct cultivar of *Argyranthemum* plant named 'OHMADMADE' characterized by its double inflorescence form with blush white-colored ray florets and cream-colored disc florets, freely branching character, dark green-colored foliage, and compact, upright and mounded growth habit.

1 Drawing Sheet

Latin name of the genus and species of plant claimed: *Argyranthemum×hybrida.*
Variety denomination: 'OHMADMADE'.

BACKGROUND OF THE INVENTION

The present invention relates to a new and distinct cultivar of *Argyranthemum* plant botanically known as *Argyranthemum×hybrida*, and hereinafter referred to by the cultivar name 'OHMADMADE'.

The new *Argyranthemum* originated in a controlled breeding program in Winmalee, New South Wales, Australia during February 2002. The objective of the breeding program was the development of *Argyranthemum* cultivars that are freely branching, have a compact and upright growth habit, are freely flowering, and have unique flower coloration.

The female (seed) parent of the new cultivar was the proprietary breeding line 01-167, not patented, which exhibits semi-double pink-colored ray florets. The male (pollen) parent of the new cultivar was proprietary breeding line 01-19, not patented, which exhibits single flower form and a very compact habit. Seed from the above stated cross was germinated and grown to maturity. One plant within the progeny was discovered and selected by the inventor on Sep. 24, 2002 in a controlled environment at Winmalee, New South Wales, Australia.

Asexual reproduction of the new cultivar by terminal stem cuttings since September 2002 at Winmalee, New South Wales, Australia and West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'OHMADMADE' as a new and distinct cultivar of *Argyranthemum* plant:

1. Double inflorescence form with white blushed with pink colored ray florets and cream-colored disc florets.

2. Dark green-colored foliage.
3. Freely branching character.
4. Compact, upright and mounded growth habit.

Plants of the new cultivar differ from plants of the female parent primarily in flower color and flower form and from the male parent primarily in flower form and growth habit.

Plants of the new cultivar are similar to the cultivar Supagem, U.S. Plant Pat. No. 13,826. However, in side-by-side comparisons, carried out at West Chicago Ill., plants of the new cultivar differ from plants of 'Supagem' in the following characteristics:

1. Plants of the new cultivar have smaller flowers than plants of 'Supagem'.
2. Plants of the new cultivar have larger leaves than plants of 'Supagem'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describe the colors of the new cultivar. The plants were grown in 10 cm pots for 13 weeks in a greenhouse at West Chicago, Ill.

DETAILED BOTANICAL DESCRIPTION

Figure 1:
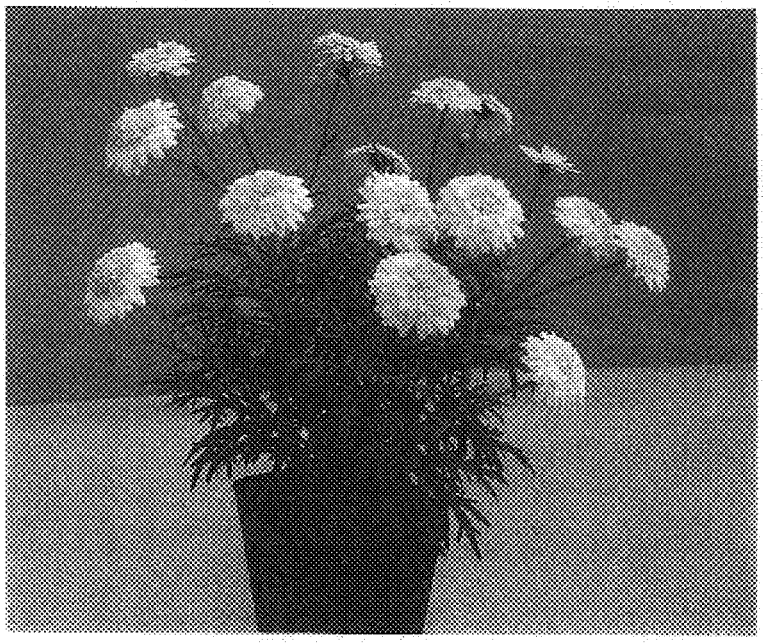
FIG. 1 illustrates a side view of the overall growth and flowering habit of 'OHMADMADE' with one plant per pot.
Figure 2:
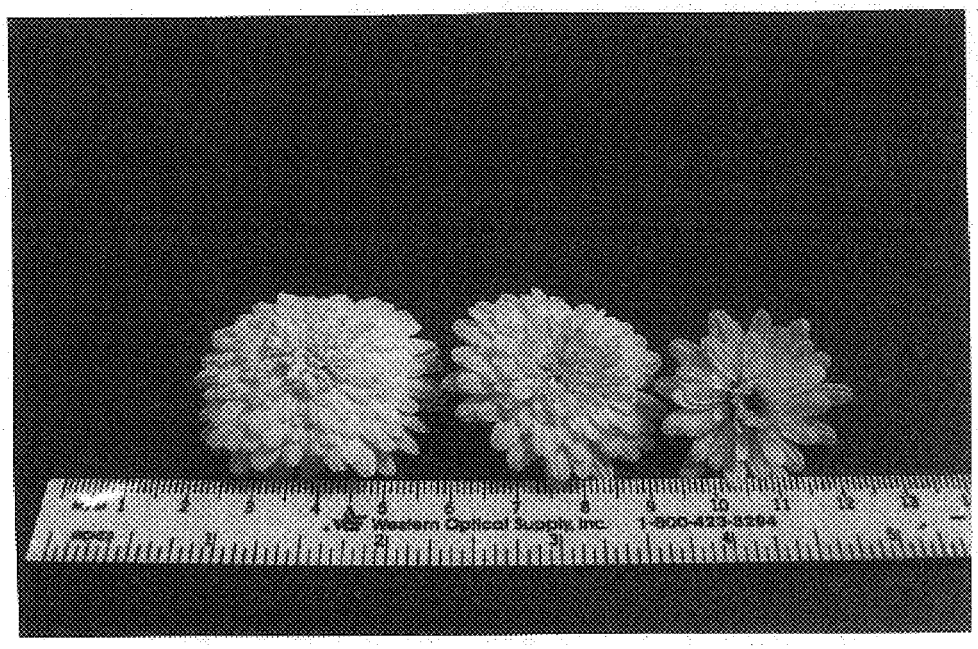
FIG. 2 illustrates a close-up view of three individual flowers of 'OHMADMADE' showing the change in color as the disc florets mature. First open on right, fully open on left.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Oct. 9, 2004 between 10:00 and 11:00 a.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 13 weeks while utilizing a soilless growth medium. Greenhouse temperatures were maintained at approximately 65°–78° F. (18°–25° C.) during the day and approximately 50°–60° F. (10°–15° C.) during the night. Greenhouse light levels were maintained at 6,000 to 9,000 footcandles during the day.

Botanical classification: *Argyranthemum×hybrida* cultivar OHMADMADE.

Parentage:

*Male parent*.—Proprietary *Argyranthemum* breeding line 01-19, not patented.

*Female parent*.—Proprietary *Argyranthemum* breeding line 01-167, not patented.

Propagation:

*Type cutting*.—Terminal stem.

*Time to initiate roots*.—Approximately 6 to 8 days.

*Time to produce a rooted cutting*.—Approximately 21 to 28 days.

*Root description*.—Fine, fibrous.

*Rooting habit*.—Freely branching.

Plant description:

*Crop time*.—Approximately 6 to 9 weeks from a rooted cutting in a 10 cm pot.

*Habit of growth*.—Compact. Freely branching. One or two pinches improve basal branching.

*Form*.—Upright, mounded.

*Size*.—Height: Approximately 25.4 cm from soil level to top of plant plane. Width (area of spread) — Approximately 28.7 cm.

*Branch*.—Quantity per plant: Approximately 9. Strength: Strong. Length from soil level to base of peduncle: Approximately 14.6 cm. Diameter: Approximately 3.5 mm. Texture: Glabrous. Color: Young and supple: 143B, mature and woody: 199B. Internode length at middle of branch: Approximately 6.2 mm.

*Foliage*.—Quantity of leaves per branch: Approximately 21. Type: Simple. Fragrance: Slight. Arrangement: Alternate. Aspect: At an acute angle to the stem. Shape: Obovate. Margin: Parted. Apex: Acute, cuspidate. Base: Attenuate. Venation pattern: Pinnate. Length: Approximately 5.1 cm. Width: Approximately 2.7 cm. Texture: Upper and lower surfaces are glabrous. Color of mature foliage: Upper surface: Darker than 146A with venation of 144A, glaucous. Lower surface: 146A with venation of 144A.

Flowering description:

*Time to first flower*.—Approximately 8 weeks from planting of rooted cutting.

*Flowering habit*.—Freely flowering under outdoor growing conditions with substantially continuous blooming from spring through autumn and year round in greenhouse environment.

Inflorescence description:

*Appearance*.—Solitary, composite. Persistent. Shape: Round. Aspect: Facing upward or outward. Disc and ray florets develop acropetally on a capitulum. Fragrance: None.

*Quantity of flowers per lateral branch*.—Approximately 4.

*Size*.—Diameter: Approximately 4.0 cm. Depth: Approximately 1.0 cm.

*Lastingness of inflorescence*.—Approximately 7–10 days.

*Bud*.—Rate of opening: Generally it takes 3–6 days for buds to progress from first color to fully open flowers. Shape: Spherical. Diameter: Approximately 6.6 mm. Depth: Approximately 6.0 mm. Color: 1D.

*Ray florets*.—Quantity per inflorescence: Approximately 70. Aspect: Ribbed. Arrangement: Imbricate at base. Shape: Elliptic. Margin: Entire. Apex: Emarginate with three tips. Base: Attenuate and fused to form tube. Length: Approximately 1.1 cm. Width: Approximately 4 mm. Texture: Glabrous and ribbed. Color of ray florets: Upper and lower surfaces: 75C when first open, gradually fading to 155D when fully open.

*Disc*.—Diameter: Approximately 1.8 cm. Depth: Approximately 9 mm.

*Disc florets*.—Quantity per inflorescence: Approximately 25 Shape: Tubular with five lobes each having an acute apex. Margin: Entire. Length: Approximately 4 mm. Diameter at apex: Approximately 1.8 mm. Diameter at base: Approximately 0.8 mm. Texture: Glabrous. Color of immature floret: 150D. Color of mature floret: 155A. Calyx: Shape: Tubular. Length: Approximately 2.3 mm. Diameter: Approximately 1.3 mm. Texture: Glabrous, papery. Color: Colorless, translucent.

*Phyllaries*.—Quantity per inflorescence: Approximately 15. Arrangement: Imbricate, arranged in several rows. Shape: Ovate. Margin: Entire. Apex: Acute. Base: Truncate. Length: Approximately 4 mm. Width: Approximately 1 mm. Texture: Glabrous, papery along edges. Color of upper surface: 143C in center, N199D and transparent along margin. Color of lower surface: 144B in center, N199D and transparent along margin.

*Peduncle*.—Strength: Strong, pliable. Aspect: Erect. Length: Approximately 7.5 cm. Diameter: Approximately 1.3 mm. Texture: Glabrous. Color: 146A, glaucous.

*Reproductive organs*.—Androecium: Present on disc florets only. Stamens: 5 fused around style. Anther length: 1.5 mm. Anther color: 9B. Amount of pollen: Moderate. Pollen color: 13A. Gynoecium: Present on ray and disc florets. There is one pistil per floret. Pistil length: 3.3 mm. Stigma shape: Two parted. Stigma length: 0.8 mm. Stigma color: 12A. Style length: 2 mm. Style color: 1D. Ovary diameter: 0.5 mm. Ovary color: N144D.

Seed and fruit production: Neither seed nor fruit production has been observed.

Disease and pest resistance: Resistance to pathogens and pests common to *Argyranthemum* has not been observed.

What is claimed is:

1. A new and distinct cultivar of *Argyranthemum* plant named 'OHMADMADE', substantially as herein shown and described.

* * * * *